US009162107B2

(12) United States Patent  (10) Patent No.: US 9,162,107 B2
Aminzade  (45) Date of Patent: Oct. 20, 2015

(54) CROWD SOURCED DISCOVERY OF MUSIC FOR IMPROVING PERFORMANCE

(71) Applicant: Google Inc., Mountain View, CA (US)

(72) Inventor: Daniel Aminzade, Menlo Park, CA (US)

(73) Assignee: Google Inc., Mountain View, CA (US)

(*) Notice: Subject to any disclaimer, the term of this patent is extended or adjusted under 35 U.S.C. 154(b) by 163 days.

(21) Appl. No.: 13/726,919

(22) Filed: Dec. 26, 2012

(65) Prior Publication Data

US 2014/0180448 A1   Jun. 26, 2014

(51) Int. Cl.
*A63B 71/00* (2006.01)
*A63B 24/00* (2006.01)
*G06Q 10/10* (2012.01)
*G06F 19/00* (2011.01)

(52) U.S. Cl.
CPC ........ *A63B 24/0021* (2013.01); *G06F 19/3481* (2013.01); *G06Q 10/109* (2013.01)

(58) Field of Classification Search
CPC .......... G06F 17/30241; G06F 19/3481; A63B 24/0021; G06Q 10/109
See application file for complete search history.

(56) References Cited

U.S. PATENT DOCUMENTS

| 7,973,231 B2 | 7/2011 | Bowen |
| 2008/0096726 A1* | 4/2008 | Riley et al. ......................... 482/8 |
| 2008/0097633 A1 | 4/2008 | Jochelson et al. |
| 2010/0279825 A1 | 11/2010 | Riley et al. |
| 2011/0016120 A1* | 1/2011 | Haughay et al. ............... 707/734 |
| 2012/0221687 A1* | 8/2012 | Hunter et al. .................. 709/219 |
| 2013/0031162 A1* | 1/2013 | Willis et al. .................... 709/203 |

OTHER PUBLICATIONS

Doyle, "Does Motivational Music Improve Athletic Performance?" Available at: http://www.education.com/science-fair/article/motivational-music-improve-athletic-performance/. Visited on: Aug. 5, 2012.
European Search Report in Application No. 13192276.7, mailed Feb. 17, 2014.

* cited by examiner

*Primary Examiner* — Tarek Chbouki
(74) *Attorney, Agent, or Firm* — Morris & Kamlay LLP

(57) ABSTRACT

Media components can be ranked based on their influence on athletic performance. A score can be computed for a media component based on an individual's athletic performance during output of that media item in comparison with the individual's athletic performance during the output of different media items, or in the absence of any media items. The score can be used to establish an overall total score for the media component by comparing the score to one or more scores received from other individuals for the same media component. The overall total score can be used to compute a ranking for the media component by comparing the media component's overall total score with the overall total score for one or more other media components.

26 Claims, 3 Drawing Sheets

CROWD SOURCED DISCOVERY OF MUSIC FOR IMPROVING PERFORMANCE

BACKGROUND

Athletic performance may be improved by implementing various techniques including delivering a selected media component to an individual. The media component may be or may be based on a song, a music video, a speech, a dialogue, a show, a movie, a genre, a tempo, keys, musical style, volume variation, instrumentation, musical era or the like. For example, listening to a certain song may result in improved athletic performance such as, but not limited to, a performance that is faster, stronger, more efficient, more desirable, longer, higher, lower, further, greater in duration, or the like. The improved performance may result from the effect of the media on the individual exposed the sound. For example, an individual may be more motivated, energized, engaged, or inclined to work harder based on a media component.

BRIEF SUMMARY

According to implementations of the disclosed subject matter, a first user's performance data during the first user's physical activity as well as the first user's performance data during a first media component's output may be determined. Here, the media component may be output during the first user's physical activity and may be a song, a music video, a speech, a dialogue, a show, a movie or the like. The physical activity may be a workout session with duration greater than the duration of the output of the media component. The performance data may be based on a user's speed, acceleration, cadence, heart rate, location, calorie count, power output, torque, energy level, perspiration, fatigue, user input, or the like. Further, the performance data may be calculated based on the user's location, such as the GPS location. A first score based on the first user's performance during the physical activity and the first user's performance during the first media component may be calculated. Further, the first score may be based on an average of the performance during the physical activity and the average of the performance during the media component's output and/or a ratio of the two. A total score for the first media component may be calculated based on the first score and a second score that may correspond to a second user. The total score may be an average of the first score and the second score. Calculating the total score may be based on a determination of whether the first score is within a predetermined range and the total score may not be computed based on if the first score is not within the predetermined range. Calculating the total score may include updating a previously calculated total score. A ranking for the first media component relative to a second media component may be received based on the total score. The ranking may be based on whether the total score for the first media component is based on at least a predetermined number of scores.

According to implementations of the disclosed subject matter, a first score may be received. The first score may be based on a first user's performance data corresponding to the first user's physical activity and the first user's performance data during a first media component's output. The first media component may be output during the first user's physical activity. A second score may be received based on a second user's performance data corresponding to the second user's physical activity and the second user's performance data during a first media component's output. The first media component may be output during the second user's physical activity. A total score may be calculated based on the first score and the second score and the first media component may be ranked relative to a second media component based on the total score.

Additional features, advantages, and implementations of the disclosed subject matter may be set forth or apparent from consideration of the following detailed description, drawings, and claims. Moreover, it is to be understood that both the foregoing summary and the following detailed description are exemplary and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

A list of media components that are ranked based on their effect on athletic performance may assist in influencing athletic performance. The ranked list may assist athletic performance by exposing an individual to media components known to influence performance in a desirable manner. A media component may be categorized by any applicable identification technique such as, but not limited to, a title, an artist, a genre, a tempo, keys, musical style, volume variation, instrumentation, musical era, or the like. Athletic performance may be measured by, but is not limited to, a user's speed, acceleration, cadence, heart rate, location, calorie count, power output, torque, energy level, perspiration, fatigue, user input, or the like. According to implementations of the disclosed subject matter, media components may be ranked based on their effect on the performance of one or more individuals.

Figure 3:
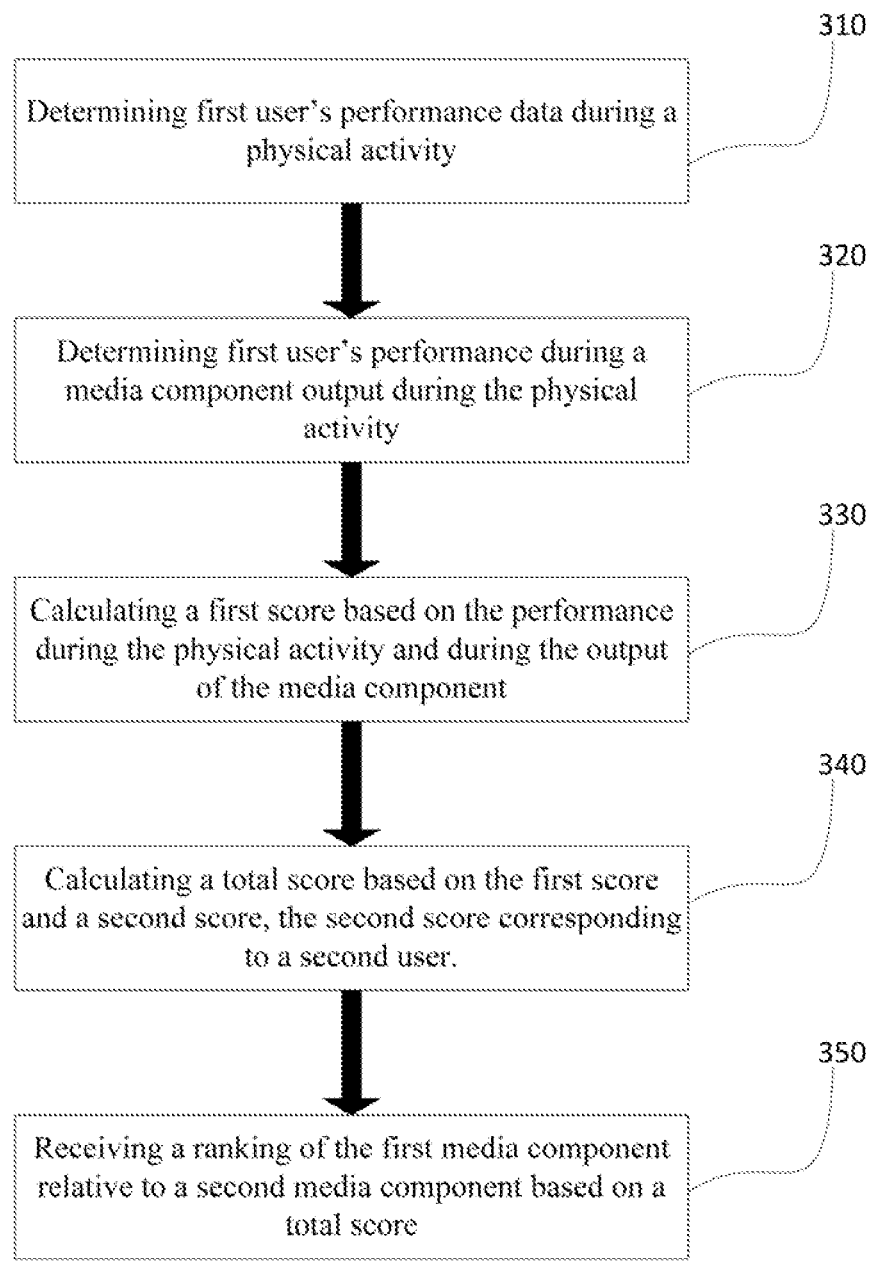
FIG. 3 shows an example process for ranking a first media component relative to a second media component.

According to implementations of the disclosed subject matter, as shown in FIG. 3 at step 310, performance data corresponding to a first user's physical activity may be determined. For example, an individual's speed during the entirety of a jog may be calculated by a speed monitoring device. Additionally, at step 320, performance data corresponding to the first user's physical activity during a media component's output may be determined. For example, an individual's speed during a portion of a jog when a specific song is being played by the user's portable media player may be calculated by a speed monitoring device. At step 330, a first score may be calculated based on the performance data determined during the physical activity and the performance data determined during the output of the media component. For example, a score may be computed by dividing the average speed of an individual during the portion of a jog when a specific song is played, by the individual's average speed during the entirety of the jog. At step 340, a total score for the first media component may be calculated based on the first score and a second score for the same media component, which was obtained for a second user. For example, a total score for a song can be calculated by averaging a first score computed during Anna's jog and a second score computed during Bella's Jog. At step 350, a ranking for the first media component relative to a second media component may be received based on the total score. For example, the total score for a first song can be compared to a total score for one or more other songs and the first song may be ranked based on the comparison (e.g., a higher total score for the first song than a second song may cause the first song to be ranked higher than the second song).

According to implementations of the disclosed subject matter, data corresponding to a user's athletic performance may be determined, as shown in step 310 of FIG. 3. A single device may be used to gather the performance data, though the device may include multiple sensor components used to obtain the performance data, such as an accelerometer, a GPS tracker, a speed tracker, a heart rate monitor, a thermometer, or the like. For example, a mobile phone capable of tracking an individual's speed based on either an accelerometer or a GPS tracker within the mobile phone may be used to gather the performance data. Alternatively, a plurality of devices may be used to gather performance data. The plurality of devices may include one or more sensors, an accelerometer, a GPS tracker such as in a GPS watch, a speed tracker, a heart rate monitor, a thermometer, a power meter or the like. For example, a tracker inside a user's shoe may be used in combination with a mobile phone to measure both speed and elevation, resulting in a calculation of performance data. Either a single device or a combination of devices used to gather performance data may collaborate with a remote device, such as a remote server or cloud-based platform, to determine the performance data. The remote device may be, but is not limited to, a server, a cloud based server, a satellite, a database, a radio, or the like. For example, a mobile phone may communicate with a cloud based service which stores user health data such as the user's weight and height. The mobile phone may use the health data received from the cloud based service to calculate user specific calorie burn rate.

According to implementations of the disclosed subject matter, as shown at step 320 of FIG. 3, a user's performance data corresponding to the user's physical activity during a media component's output may be determined. The determination may be made by tracking each media component output and the corresponding performance that occurs during the time that the media component is output. For example, if a user, while jogging, listens to ten different songs using a portable media device, performance data collected during each song may be tracked separately. Alternatively, for example, if the user listens to ten different songs using the portable media device, performance data for the entire jog as well as performance data collected specifically during at least one song may be tracked. The user's media component exposure relative to performance may be determined using a media device. The media device may be the same device that determines or helps determine user performance data. For example, a user may use a mobile phone to play music throughout the user's jog. The mobile phone may also use a built in accelerometer and/or speed sensor to gather the user's speed during the jog. Thus, the mobile phone can track overall performance data as well as performance data during individual songs. Alternatively, the media device may operate in conjunction with one or more different devices to determine media component exposure relative to performance. The one or more devices may communicate with the media device via any applicable communication technique such as, but not limited to, a wired connection, a wireless connection such as Bluetooth, Wi-Fi, infrared, Near Field Communication, or the like. For example a sensor inside a user's shoe may track the user's speed and/or distance traveled. The sensor may be connected to the user's portable media player via a Bluetooth connection and either the portable media player or the sensor may record performance and media component data related to each other. Alternatively, the media device may operate in conjunction with a remote device to determine media component exposure relative to performance. The remote device may be, but is not limited to, a server, a cloud based service, a satellite, a database, a radio, or the like. For example, a user's mobile phone may use a signal from a GPS satellite to track the user's position and/or speed and may play songs for the user during a jog. The mobile phone may track the user's position and/or speed in relation to specifically one or more of the songs as well as the user's position and/or speed during the entire jog. According to implementations of the disclosed subject matter, the media component exposure and the performance data may be matched by any applicable technique including, but not limited to, time based synchronization, GPS based synchronization, manual synchronization, automatic software based synchronization, or the like. For example, a mobile phone used both to play the media component and track a user's speed may relate the speed to one or more respective songs by automatically matching the speed to the one or more songs using applicable software stored on the mobile phone. Alternatively, a user may manually match a chunk of performance data to a specific song based on a set of performance data and songs provided to the user.

According to implementations of the disclosed subject matter, as shown in step 330 of FIG. 3, a score may be computed for a media component based on a user's physical performance during the output of the media component. For example, a user may listen to the song "Dashing" during a particular portion of the user's jog. Accordingly, the song "Dashing" may receive a score based on the user's performance during the portion of the jog that the song was played to the user. The score may be based on a comparison between a user's performance during the output of a media component and the user's performance in addition to or separate from the user's performance during the output of the media component. The user's performance during the output of the media component may be compared to the user's performance for a duration of the physical activity greater than and including the media component output. Accordingly, a score for the media component may be calculated such that (media_comp*(media_comp+X)), wherein media_comp corresponds to performance data collected during the output of a media component, * corresponds to an operation or a ratio and X represents performance data for a duration of time greater than 0 not including the performance data during the output of the media component. Typically, the operation used to calculate the score is a division or ratio calculation though, more generally, any applicable operation may be used. For example, a user may use a mobile phone to listen to a plurality of songs including "Passing you by" during a jog and the phone may track the user's speed throughout the jog. The song "Passing you by" may receive a score based on the user's average speed during the song divided by the user's average speed during three songs including the songs directly before and after "Passing you by" as well as the song itself. As an alternate example, the song "Passing you by" may receive a score based on the user's average speed during the song divided by the user's average speed for the entire workout while measurements were taken by the mobile phone.

Alternatively, the score may be based on the comparison of a user's performance during the output of a media component and the user's performance during a physical activity, excluding the performance data collected during output of the media component. Accordingly, a score for the media component may be calculated such that (media_comp*(X!media_component)), wherein media_comp corresponds to performance data collected during the output of a media component, * corresponds to an operation or a ratio. X!media_component represents performance data for a duration of time greater than 0, excluding performance data collected during the output of the media component. Typically, the operation used to calculate the score is a division or ratio calculation though, more generally, any applicable operation may be used. For example, a user may use a mobile phone to listen to a plurality of songs including "Zipping and Zapping" during a jog and the phone may track the user's speed throughout the jog. The song "Zipping and Zapping" may receive a score based on the user's average speed during the song divided by the user's average speed at least during the song directly before and directly after "Zipping and Zapping" but excluding the user's speed during the song "Zipping and Zapping" itself. As an alternate example, the song "Zipping and Zapping" may receive a score based on the user's average speed during the song divided by the user's average speed for the entire workout excluding measurements taken during the output of the song "Zipping and Zapping".

Figure 4:
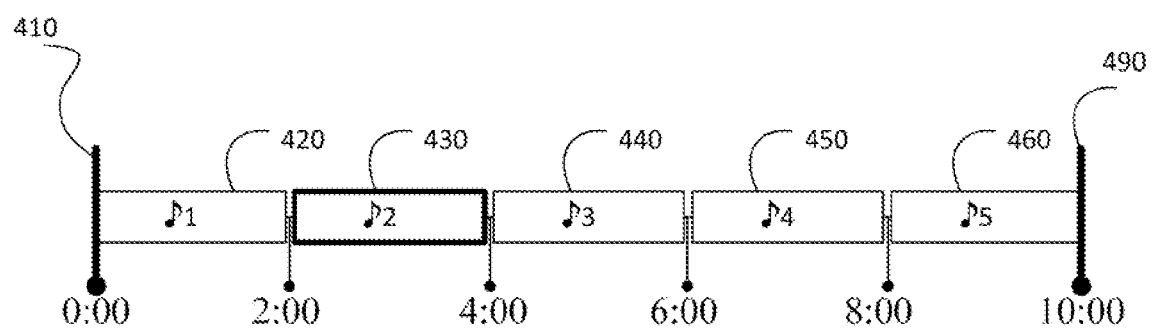
FIG. 4 shows an example visualization corresponding to media output during a physical activity.

FIG. 4 shows an illustration of an example media component played during a user's physical activity. The user's physical activity may begin 410 at a time 0:00 and may end 490 at time 10:00. The user may be exposed to song 1 420, song 2 430, song 3 440, song 4 450, and song 5 460 during the duration of her workout, each song lasting two minutes. Table 1 shows performance values corresponding to each song. In this example, the user's speed is taken as the measure of performance, though more generally any performance metric may be used.

As an example, a score for song 2 may be computed. The score may be computed by dividing the average speed of the user during the song (between 2:00 and 4:00) (i.e., 5) by the average speed of the user during the entire workout (between 0:00 and 10:00) (i.e., 4) to result in a score of 1.25 for song 2. Alternatively, the score may be computed dividing the average speed of the user during the song (between 2:00 and 4:00) (i.e., 5) by the average speed of the user during the entire workout excluding song 2 (between 0:00 and 2:00 as well as between 4:00 and 10:00) (i.e., 3.75) to result in a score of 1.33 for song 2.

TABLE 1

| Song (Duration: 2:00 min each) | Average Speed (mph) |
|---|---|
| ♪1 | 4.5 |
| ♪2 | 5 |
| ♪3 | 3 |
| ♪4 | 4 |
| ♪5 | 3.5 |

In another illustrative example, an individual may exercise for 30 minutes. Throughout the workout, the individual may be connected to a heart rate monitor. During the 30 minute exercise session, the individual uses her portable media player to listen to six songs, including the song "Lift Higher". While listening to "Lift Higher", the individual's heart rate may average 165 beats per minute (BPM). Additionally, the individual's average heart rate for the time 5 minutes before, during, and 5 minutes after "Lift Higher" may be 150 BPM. More specifically, if "Lift Higher" plays for 5 minutes starting at the 15 minute mark in the individual's exercise session, then the average heart rate of 150 BPM can correspond to time ranging from the 10 minute mark through the 25 minute mark. The score corresponding to "Lift Higher" can be computed by dividing 165 BPM (i.e., the average heart rate during "Lift Higher") by 150 BPM (i.e., the average heart rate during the ±5 minute range relative to the playback of "Lift Higher"). Accordingly, the score for "Lift Higher" would be 1.1.

According to implementations of the disclosed subject matter, a performance value corresponding to a media component (e.g., speed, distance, etc.) may be excluded from the calculation of a score for the media component if the value is an outlier. A performance value may be an outlier based on the variation of the performance value by a predetermined threshold. Excluding performance value outliers may improve the quality of the overall score as an outlier may likely result from an extrinsic or unrelated event such as, but not limited to, a drastic change in slope, a resting period, a dangerous situation, an external motivating factor, a milestone point, or the like. For example, if the predetermined threshold is 25%, then an outlier may be any performance value that is either less than or greater than 25% of an average. An average may be the average performance value for a duration of time greater than the output duration of the media component such that it includes the media component. In an illustrative example, Table 2 shows five songs played during a user's jog and the corresponding average user speed during the respective songs. Here, the variation threshold is set to 25%, and the average speed for the entire physical activity is 3.98 mph. Accordingly, as shown in column 3, none of the songs are outliers as the variation for each song is less than 25%. Alternatively, the average may be the average performance value for a duration of time excluding the performance during the duration of the media component. In an illustrative example, Table 2 shows five songs played during a user's jog and the corresponding average user speed during the respective songs. Here, the variation threshold can be set to 25%, and the average speed including the entire physical activity may vary for each song as the average speed during the subject song will be excluded. Column 4 shows the variation values corresponding to each song, calculated based on an average speed excluding the subject song. Accordingly, as shown in column 4, song 2 and song 3 are outliers as the variation for each song is greater than 25%. Notably, song 2 is an outlier due to a high performance variation value as the speed during song 2 (4.9 mph) was higher than the average speed (3.75 mph) and song 3 is an outlier due to a low performance variation value as the speed during song 3 (3 mph) was lower than the average speed (4.23 mph). Accordingly, song 2 and song 3 may be excluded from the calculation of scores for songs 1, 4, and 5.

According to implementations of the disclosed subject matter, a threshold value may adjust based on the amount of the sample size. A smaller sample size may result in a lower threshold such that more deviation from an average may be acceptable. A larger sample size may adjust to a higher threshold such that less deviation from an average may be acceptable. Continuing the previous example, the original threshold value may adjust from 25% to 60% based on the exclusion of songs 2 and 3 from table two.

TABLE 2

| Song (Duration: 2:00 min each) | Average Speed (mph) | Variation (Including all songs) | Variation (excluding the respective song) |
|---|---|---|---|
| ♪1 | 4 | 1% | .6% |
| ♪2 | 4.9 | 23% | 30% |
| ♪3 | 3 | 24.6% | 29% |
| ♪4 | 4.5 | 13% | 17% |
| ♪5 | 3.5 | 12% | 16% |

According to implementations of the disclosed subject matter, the score for a specific media component calculated during an athletic performance session may be compared with at least one other media component score for the same media component, which is collected during a different performance session or a different individual's session. The comparison may be conducted at a central device, such as, but not limited to, a server, a database, a central account or the like. The central device may receive at least two or more scores for the same media component. Each media component may have unique component identification and the central device may utilize the unique component identification to associate two or more scores received for the same media component. The comparison of the two or more scores may be an average, a trend match, a ratio, or any other suitable operation. Additionally, the comparison may result in a total score for the media component and the total score may be updated based on one or more scores. For example, a beat with a tempo of 140 BPM, and only a beat with a tempo of 140 BPM, may be identified by a hexadecimal value 0x3F7A83. The score, 1.3, computed for a beat with the tempo of 140 BPM calculated during Alan's workout may be sent to a music server by Alan's MP3 player along with 0x3F7A83, the value identifying the beat. Additionally, a score, 1.2, for the beat with the tempo of 140 BPM computed during Bob's workout may also be sent to the music server by Bob's mobile phone along with the same 0x3F7A83, the value identifying the beat. The score, 1.3, received from Alan and the score, 1.2, received from Bob may be averaged, resulting in a total score of 1.25. Continuing the example, if the music server receives a score of 1.5 corresponding to Charles' workout while exposed to the beat with the tempo of 140 BPM, then the music server may update the previous total score of 1.25 by averaging all three scores (i.e., (1.3+1.2+1.5)/3), resulting in an updated total score of 1.33.

According to implementations of the disclosed subject matter, a score corresponding to a media component (e.g., song, beat, sound, etc.) may be excluded from the calculation of a total score for the media component if the score is an outlier. A score may be an outlier based on the variation of the score by a predetermined threshold value. Excluding outlying scores may improve the quality of the total score as an outlier may likely result from an extrinsic or unrelated event such as, but not limited to, a drastic change in slope, a resting period, a dangerous situation, an external motivating factor, a milestone point, or the like. For example, music server may generate or update a total score based on a new score if the new score is within 25% of the established total score or within 25% of a predetermined value. In a specific example, the musical genre Heavy Metal may have a current total score of 1.3 based on 10 scores received by a music server. If the music server receives a new score of 1.65 from a user Dave, the server may reject the new score and not adjust the existing score of 1.3 as 1.65 is greater than a 25% deviation from the current score. However, if the music server receives a new score of 1.4 from a user Ethan, then the server may adjust the current score of 1.3 by incorporating the new score of 1.4 as 1.4 is within 25% of 1.3. The adjustment may be made by averaging the 10 original scores with the new score such that (1.3×10+1.4)/11. Accordingly, the adjusted score can be 1.31.

According to implementations of the disclosed subject matter, the central device may rank media components based on the total score for the media component. The ranking may be adjustable and may dynamically adjust based on updated media component scores. For example, a music server may determine total scores for 10 different songs, the total scores based on user speeds while jogging. The music server may rank the songs based on their total scores and organize a list from highest ranked to lowest ranked song. The highest ranked song can be the song with the highest total score, and may be the song that most corresponds to faster user speeds while jogging. The ranking may be organized by type of media component. For example, a central device may rank songs, tempos, and genres separately. Accordingly, there may be 10 songs, 15 tempos, and 12 genres, all with respective rankings in their category. The central device may generate one or more playlist based on the ranked media component. One or more of the playlists may be provided to a user device, and may be categorized based on media type. For example, a user may communicate with a media server using a mobile phone and request motivational media component prior to a workout session. The media server can send the user the most recent top 10 ranked media component. Additionally, the user may specify that she requires songs in a certain genre or may require that she wants the number one song across all genres. Accordingly, the media server may transmit the requested songs or a list of the songs to the user.

According to implementations of the disclosed subject matter, a media component may not be approved for ranking unless a threshold size is established. The threshold size may be the number of scores applied to establish a total score for the media component. If a threshold number of scores is not met, a central device may store the scores indefinitely or for a limited amount of time. For example, the threshold size for a number of scores may be 10 scores. A music server may receive seven scores from seven different users for the song "Not enough" and calculate a total score for the song based on the seven scores. Accordingly, because the number of scores that contribute to the total score does not meet the threshold value of 10, the song "Not enough" may not ranked by the music server. The music server may store the seven scores until additional scores are provided.

Figure 1:
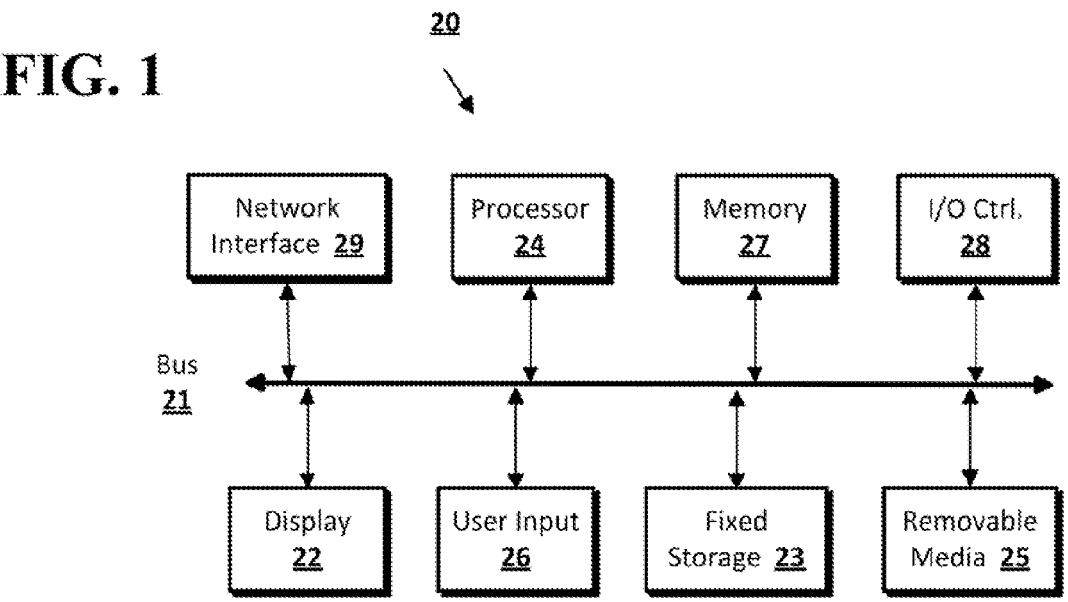
FIG. 1 shows a computer according to an implementation of the disclosed subject matter.

Implementations of the presently disclosed subject matter may be implemented in and used with a variety of component and network architectures. FIG. 1 is an example computer 20 suitable for implementing implementations of the presently disclosed subject matter. The computer 20 includes a bus 21 which interconnects major components of the computer 20, such as a central processor 24, a memory 27 (typically RAM, but which may also include ROM, flash RAM, or the like), an input/output controller 28, a user display 22, such as a display screen via a display adapter, a user input interface 26, which may include one or more controllers and associated user input devices such as a keyboard, mouse, and the like, and may be closely coupled to the I/O controller 28, fixed storage 23, such as a hard drive, flash storage, Fibre Channel network, SAN device, SCSI device, and the like, and a removable media component 25 operative to control and receive an optical disk, flash drive, and the like.

The bus 21 allows data communication between the central processor 24 and the memory 27, which may include read-only memory (ROM) or flash memory (neither shown), and random access memory (RAM) (not shown), as previously noted. The RAM can include the main memory into which the operating system and application programs are loaded. The ROM or flash memory can contain, among other code, the Basic Input-Output system (BIOS) which controls basic hardware operation such as the interaction with peripheral components. Applications resident with the computer 20 can be stored on and accessed via a computer readable medium, such as a hard disk drive (e.g., fixed storage 23), an optical drive, floppy disk, or other storage medium 25.

The fixed storage 23 may be integral with the computer 20 or may be separate and accessed through other interfaces. A network interface 29 may provide a direct connection to a remote server via a telephone link, to the Internet via an internet service provider (ISP), or a direct connection to a remote server via a direct network link to the Internet via a POP (point of presence) or other technique. The network interface 29 may provide such connection using wireless techniques, including digital cellular telephone connection, Cellular Digital Packet Data (CDPD) connection, digital satellite data connection or the like. For example, the network interface 29 may allow the computer to communicate with other computers via one or more local, wide-area, or other networks, as shown in FIG. 2.

Many other devices or components (not shown) may be connected in a similar manner (e.g., document scanners, digital cameras and so on). Conversely, all of the components shown in FIG. 1 need not be present to practice the present disclosure. The components can be interconnected in different ways from that shown. The operation of a computer such as that shown in FIG. 1 is readily known in the art and is not discussed in detail in this application. Code to implement the present disclosure can be stored in computer-readable storage media such as one or more of the memory 27, fixed storage 23, removable media 25, or on a remote storage location.

Figure 2:
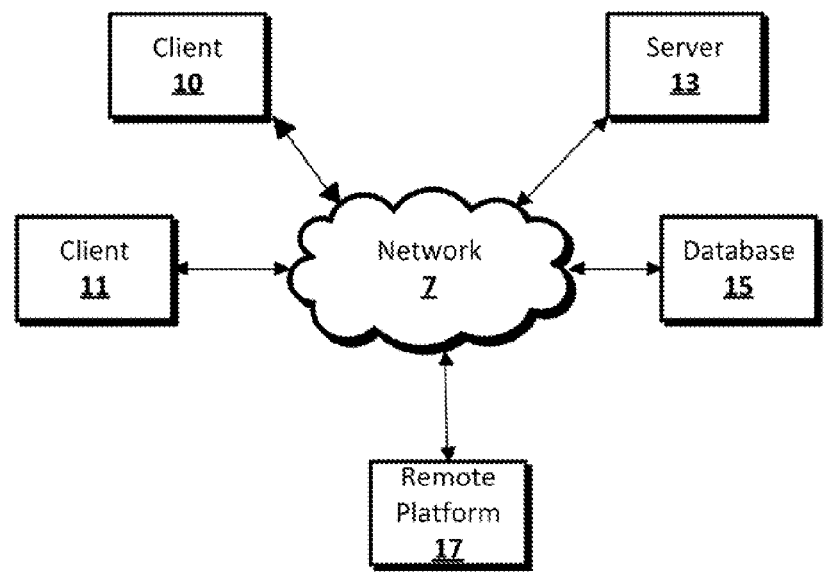
FIG. 2 shows a network configuration according to an implementation of the disclosed subject matter.

FIG. 2 shows an example network arrangement according to an implementation of the disclosed subject matter. One or more clients 10, 11, such as local computers, smart phones, tablet computing devices, and the like may connect to other devices via one or more networks 7. The network may be a local network, wide-area network, the Internet, or any other suitable communication network or networks, and may be implemented on any suitable platform including wired and/or wireless networks. The clients may communicate with one or more servers 13 and/or databases 15. The devices may be directly accessible by the clients 10, 11, or one or more other devices may provide intermediary access such as where a server 13 provides access to resources stored in a database 15. The clients 10, 11 also may access remote platforms 17 or services provided by remote platforms 17 such as cloud computing arrangements and services. The remote platform 17 may include one or more servers 13 and/or databases 15.

More generally, various implementations of the presently disclosed subject matter may include or be implemented in the form of computer-implemented processes and apparatuses for practicing those processes. Implementations also may be implemented in the form of a computer program product having computer program code containing instructions implemented in non-transitory and/or tangible media, such as floppy diskettes, CD-ROMs, hard drives, USB (universal serial bus) drives, or any other machine readable storage medium, wherein, when the computer program code is loaded into and executed by a computer, the computer becomes an apparatus for practicing implementations of the disclosed subject matter. Implementations also may be implemented in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing implementations of the disclosed subject matter. When implemented on a general-purpose microprocessor, the computer program code segments configure the microprocessor to create specific logic circuits. In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions. Implementations may be implemented using hardware that may include a processor, such as a general purpose microprocessor and/or an Application Specific Integrated Circuit (ASIC) that implements all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

In situations in which the systems discussed here collect personal information about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A method comprising:
    determining, with a processor in connection with a database, a first user's performance data corresponding to the first user's workout session during a first media component output;
    calculating, with the processor, a first score based on an average of the first user's performance data during the first user's workout session and an average of the first user's performance data during the first media component's output;

and receiving, with the processor, a ranking of the first media component relative to a second media component, wherein the second media component includes a score based upon physical performance data similar to those associated with the first media component, the ranking based on:
a total score for the first media component, wherein the total score is calculated based on the first score and a second score, the second score is based on an average of a second user's performance data corresponding to the second's workout session during the first media component's output,
wherein the first media component is approved for the ranking when the total score for the first media component is greater than a threshold number.

2. The method of claim 1, wherein the duration of the workout session is greater than the duration of the first media component's output.

3. The method of claim 1, wherein calculating the total score based on the first score and the second score further comprises averaging, with the processor, the first score and the second score.

4. The method of claim 1, wherein performance data is selected from a group consisting of a user's speed, acceleration, cadence, heart rate, location, calorie count, power output, torque, energy level, perspiration, fatigue, and user input.

5. The method of claim 1, wherein the media component is selected from a group consisting of a song, a music video, a speech, a dialogue, a show, and a movie.

6. The method of claim 1, further comprising calculating, with the processor, the first score based on a ratio of the first user's performance data during the first user's workout session and the first user's performance data during the first media component's output.

7. The method of claim 1, wherein the performance data is calculated based on the user's location.

8. The method of claim 7, wherein the user's location is calculated based on the user's GPS location.

9. The method of claim 1, wherein calculating a total score further comprises:
determining, with the processor, whether the first score is within a predetermined range; and calculating, with the processor, the total score based on the first score based on the determination.

10. The method of claim 9, wherein the total score is not based on the first score if the first score is not within the predetermined range.

11. The method of claim 1, wherein calculating the total score further comprises updating, with the processor, a previously calculated total score.

12. The method of claim 1, wherein ranking the first media component relative to a second media component based on the total score further comprises ranking the first media component if the total score is based on at least a predetermined number of scores.

13. A method comprising:
receiving a first score with a processor in connection with a database, wherein the first score is calculated by the processor based on:
a first user's performance data corresponding to the first user's workout session during a first media component's output;
receiving a second score with the processor, wherein the second score is calculated by the processor based on:
a second user's performance data corresponding to the second user's workout session during the first media component's output;
calculating, with the processor, a total score by averaging the first score and the second score;
and ranking, with the processor, the first media component relative to a second media component based on the total score and according to characteristics similar to those associated with the first media component,
wherein the first media component and the second media component are approved for the ranking when the total score for the first media component is greater than a threshold number.

14. The method of claim 13, wherein the duration of the workout session is greater than the duration of the first media component's output.

15. The method of claim 13, wherein performance data is selected from a group consisting of a user's speed, acceleration, cadence, heart rate, location, calorie count, power output, torque, energy level, perspiration, fatigue, and user input.

16. The method of claim 13, wherein the media component is selected from a group consisting of a song, a music video, a speech, a dialogue, a show, and a movie.

17. The method of claim 13, further comprising calculating, with the processor, the first score based on the average of the first user's performance data during the first user's workout session and the average of the first user's performance data during the first media component's output.

18. The method of claim 13, further comprising calculating, with the processor, the first score based on a ratio of the first user's performance data during the first user's workout session and the first user's performance data during the first media component's output.

19. The method of claim 13, wherein the performance data is calculated based on the user's location.

20. The method of claim 19, wherein the user's location is calculated based on the user's GPS location.

21. The method of claim 13, wherein calculating a total score further comprises:
determining, with the processor, whether the first score is within a predetermined range; and
calculating the total score based on the first score based on the determination.

22. The method of claim 21, wherein the total score is not based on the first score if the first score is not within the predetermined range.

23. The method of claim 13, wherein calculating the total score further comprises updating, with the processor, a previously calculated total score.

24. The method of claim 13, wherein ranking the first media component relative to a second media component based on the total score further comprises ranking, with the processor, the first media component if the total score is based on at least a predetermined number of scores.

25. A system comprising:
a database storing performance data corresponding to a first user's workout session
a processor in connection with said database, said processor configured to:
determine the first user's performance data corresponding to the first user's workout session during a first media component's output;
calculate a first score based on the first user's performance data during the first media component's output; and
receive a ranking of the first media component relative to a second media component, wherein the second media component includes a score based upon physical performance data similar to those associated with the first media component, the ranking based on:

a total score for the first media component, wherein the total score is calculated based on an average of the first score and a second score, the second score is based on a second user's performance data corresponding the second user's workout session during the first media component's output, wherein the first media component is approved for the ranking when the total score for the first media component is greater than a threshold number.

26. A system comprising:
a database storing scores;
a processor in connection with said database, said processor configured to:
- receive a first score, wherein the first score is calculated based on determining a first user's performance data corresponding to the first user's workout session during a first media component's output;
- receive a second score, wherein the second score is calculated based on determining a second user's performance data corresponding to the second user's workout session during the first media component's output that is similar to that associated with the first media component;
- calculate a total score based on an average of the first score and the second score;
- and rank the first media component relative to a second media component based on the total score, wherein the second media component includes a score based upon physical performance data, wherein the first media component is approved to rank when the total score for the first media component is greater than a threshold number.

* * * * *